(12) United States Patent
Samproni

(10) Patent No.: US 9,945,804 B2
(45) Date of Patent: Apr. 17, 2018

(54) SENSOR ARRAY

(71) Applicant: Siemens Healthcare Diagnostics Inc., Tarrytown, NY (US)

(72) Inventor: Jennifer A. Samproni, Braintree, MA (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 0 days.

(21) Appl. No.: 15/325,307

(22) PCT Filed: Jul. 17, 2015

(86) PCT No.: PCT/US2015/040837
§ 371 (c)(1),
(2) Date: Jan. 10, 2017

(87) PCT Pub. No.: WO2016/011308
PCT Pub. Date: Jan. 21, 2016

(65) Prior Publication Data
US 2017/0184532 A1    Jun. 29, 2017

(51) Int. Cl.
G01N 27/403    (2006.01)
G01N 27/327    (2006.01)
G01N 27/27     (2006.01)

(52) U.S. Cl.
CPC ......... *G01N 27/27* (2013.01); *G01N 27/3272* (2013.01)

(58) Field of Classification Search
CPC .................................. G01N 27/3272
See application file for complete search history.

(56) References Cited

U.S. PATENT DOCUMENTS

| | | | |
|---|---|---|---|
| 6,033,866 A | 3/2000 | Guo et al. | |
| 7,824,529 B2 | 11/2010 | Lauks | |
| 8,506,778 B2 | 8/2013 | Lauks | |
| 8,728,288 B2 | 5/2014 | Aas et al. | |

(Continued)

FOREIGN PATENT DOCUMENTS

| | | |
|---|---|---|
| WO | 2013163120 A1 | 10/2013 |
| WO | 2014037688 A1 | 3/2014 |

OTHER PUBLICATIONS

International Search Report and Written Opinion of International Application No. PCT/US2015/040837 dated Oct. 23, 2015.

(Continued)

*Primary Examiner* — Alexander S Noguerola
(74) *Attorney, Agent, or Firm* — Kyle D. Petaja

(57) ABSTRACT

In one illustrative embodiment, a test strip with a first planar substrate has coplanar electrodes on a first planar surface and a second planar substrate (which opposes the first surface of the first planar substrate) has coplanar electrodes on a second planar surface. The first planar surface of the first planar substrate having a first sensing area electrically connected to a first electrical contact. The second planar surface of the second planar substrate having a second electrical contact electrically connected to the first electrical contact via a conductive element, the conductive element extending between the first surface of the first planar substrate and the second surface of the second planar substrate without passing through the first planar substrate, the second planar substrate, or any intermediate layers.

7 Claims, 4 Drawing Sheets

(56) References Cited

U.S. PATENT DOCUMENTS

| | | |
|---|---|---|
| 2003/0102213 A1 | 6/2003 | Gotoh et al. |
| 2004/0005721 A1* | 1/2004 | Tanike .................. C12Q 1/001 436/518 |
| 2009/0026074 A1* | 1/2009 | Iyengar .............. G01N 27/3272 204/400 |
| 2010/0126884 A1 | 5/2010 | Wang et al. |
| 2012/0267245 A1 | 10/2012 | Chambers et al. |
| 2013/0105074 A1 | 5/2013 | Riggles et al. |

OTHER PUBLICATIONS

European Search Report and Written Opinion of European Application No. 15822391.7 dated Sep. 1, 2017.

\* cited by examiner

SENSOR ARRAY

The subject application claims benefit under 35 USC § 119(e) of U.S. provisional Application No. 62/025,632, filed Jul. 17, 2014. The entire contents of the above-referenced patent application are hereby expressly incorporated herein by reference.

BACKGROUND

This disclosure relates to a sensing device which allows for multiple tests to be run concurrently using a small sample volume.

SUMMARY OF THE INVENTIVE CONCEPT(S)

In one illustrative embodiment, the inventive concepts disclosed herein are directed to a test strip with a first planar substrate with electrodes on a first planar surface and a second planar substrate with coplanar electrodes on a second planar surface. The first planar substrate and the second planar substrate are arranged such that the first surface of the first planar substrate opposes the second planar surface of the second planar substrate. The test strips also contains an intermediate layer(s) disposed in between the opposed first surface of the first planar substrate and the second planar surface of the second planar substrate. The first planar surface of the first planar substrate having a first sensing area electrically connected to a first electrical contact. The second planar surface of the second planar substrate having a second electrical contact electrically connected to the first electrical contact via a conductive element, the conductive element extending between the first surface of the first planar substrate and the second surface of the second planar substrate without passing through the first planar substrate or the second planar substrate.

BRIEF DESCRIPTIONS OF THE DRAWINGS

DETAILED DESCRIPTION OF THE INVENTIVE CONCEPT(S)

Figure 1:
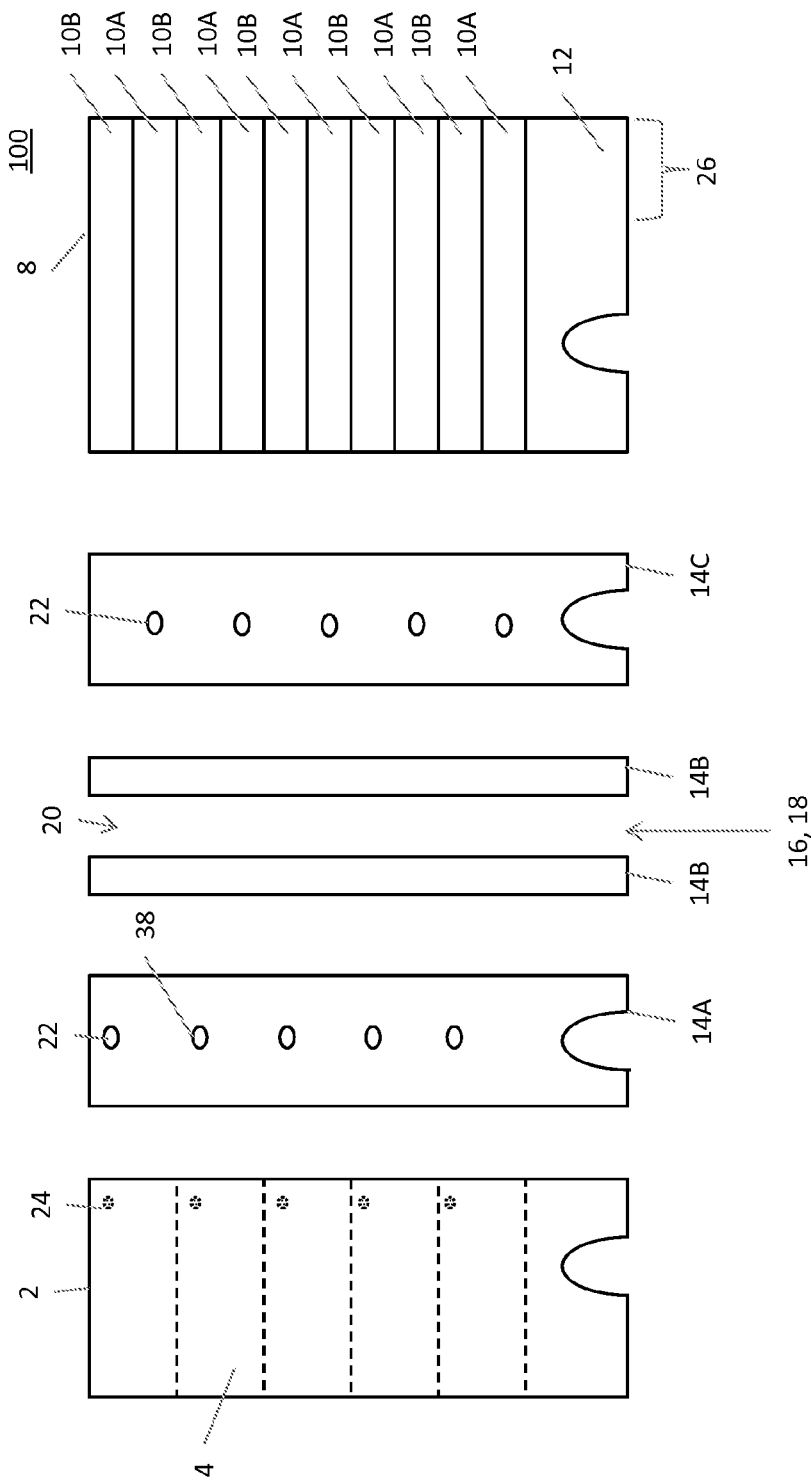
FIG. 1 depicts an exploded view of one embodiment of the test strip.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, settling or precipitation of cells or particles out of suspension or solution, chemical or biological degradation of solutions over time, stress exerted on structures, and combinations thereof, for example.

As used herein, the term "sample" and variations thereof is intended to include biological tissues, biological fluids, chemical fluids, chemical substances, suspensions, solutions, slurries, mixtures, agglomerations, tinctures, slides, powders, or other preparations of biological tissues or fluids, synthetic analogs to biological tissues or fluids, bacterial cells (prokaryotic or eukaryotic), viruses, single-celled organisms, lysed biological cells, fixed biological cells, fixed biological tissues, cell cultures, tissue cultures, genetically engineered cells and tissues, genetically engineered organisms, and combinations thereof, for example.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The inventive concepts disclosed herein are generally directed to the need to minimize the sample volume required to test two or more analytes concurrently. Low sample volumes are desirable when the sample is limited, such as in the case of neonatal patients, or when the sample itself is expensive. As opposed to prior art test strip configurations, which required the volume to increase with the number of analytes being detected, the required sample volume can be greatly reduced when the sensors are arranged in such a way that they are facing one another in a sandwich configuration (also referred to as an opposing sensor array) rather than in a coplanar configuration. However, in order to simplify the manner in which test strips with opposing sensor arrays interface with medical instruments, respective sensors can be electrically connected to coplanar (e.g., same side) contacts. This configuration maximizes the number of sensors that can be incorporated into a single test strip while simplifying the manner in which the strip interfaces with the medical instrument. Illustrative embodiments of opposing sensor arrays with coplanar contacts are discussed in connection with FIGS. 1 through 7 below.

Figure 3:
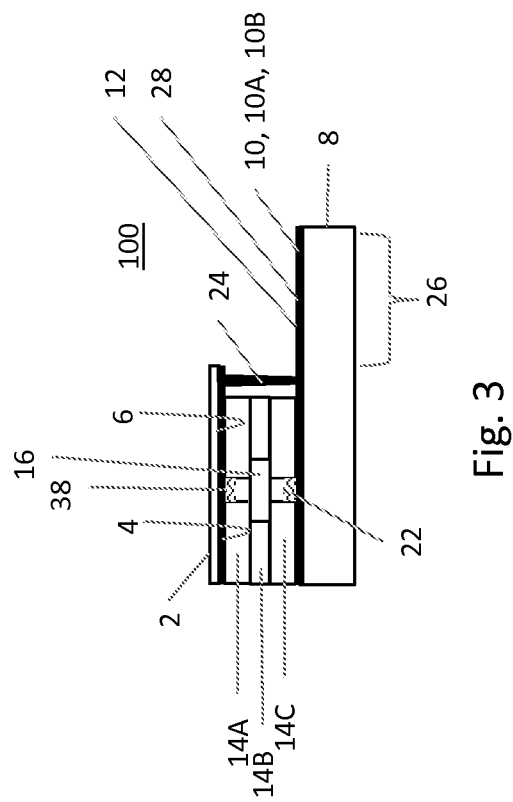
FIG. 3 depicts a side view of one embodiment of the test strip.
Figure 2:
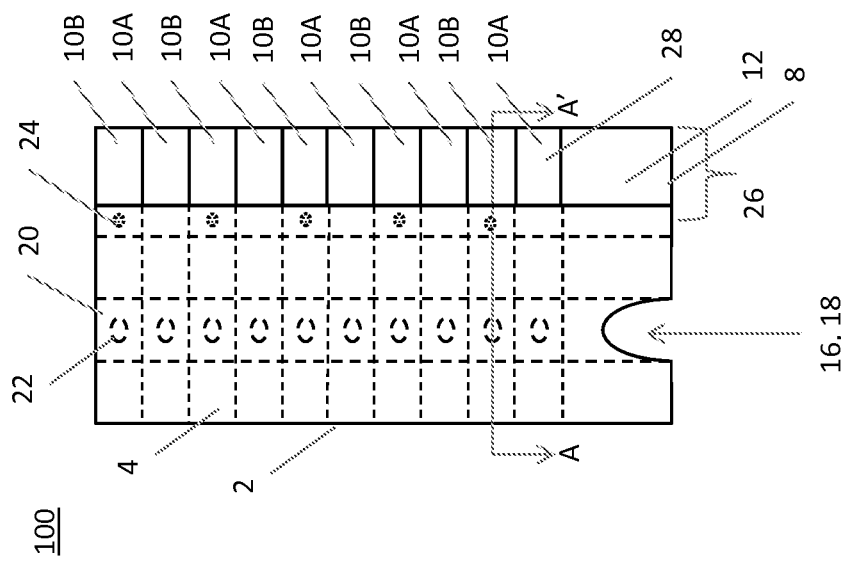
FIG. 2 depicts a top view of test strip of one embodiment of the test strip.

FIGS. 1-3 depict illustrative test strip 100. FIG. 1 depicts an exploded view of each layer of test strip 100. FIG. 2 depicts a top view of test strip 100. FIG. 3 depicts a side view of test strip 100 along line A-A'.

Test strip 100 contains a first planar substrate 2 with coplanar electrodes 4 on a first planar surface 6 and a second planar substrate 8 with coplanar electrodes 10 on a second planar surface 12. The first planar substrate 2 and the second planar substrate 8 are arranged such that the first surface 6 of the first planar substrate 2 opposes (i.e., is opposite) the second planar surface 12 of the second planar substrate 8. In this opposed configuration, the first planar surface 6 as well as the coplanar electrodes 4 disposed thereon face the second planar surface 12 and the coplanar electrodes 10 disposed thereon. Stated differently, the second planar substrate 8 is disposed below the first planar substrate 2 along a line extending from the first planar surface 6 of the first planar substrate 2 to the second planar surface 12 of the first planar substrate 2.

Planar substrates 2 and 8 may be formed using a variety of methods and materials known to a person of ordinary skill in the art. For example, planar substrates 2 and 8 may be flexible or rigid and may be constructed using, for example, standard PCB, flex PCB, PET, PI, ceramic, glass, etc.

Coplanar electrodes 4 and 10 may be formed using a variety of methods and materials known to a person of ordinary skill in the art. For example, coplanar electrodes 4 and 10 may be formed using a thick film approach (e.g., screen printing, rotogravure, pad printing, stenciling, ink jetting or aerosol jetting conductive material such as carbon, Cu, Pt, Pd, Au, and/or Nanotubes (such as carbon nanotubes), etc. . . . ) or a thin film approach (e.g., by sputtering, thermal spraying, and/or cold spraying conductive material). Coplanar electrodes 4 and 10, respectively, may be partitioned using, for example, laser ablation. It should be understood that the configuration of electrodes 4, 10 depicted herein are merely for illustrative purposes only and a person of ordinary skill in the art will appreciate that electrodes 4, 10 may be distributed on substrates 2, 8 in a variety of ways. As will be appreciated by those skilled in the art, the term "coplanar," as used herein to describe electrodes 4 and 10, should be understood as encompassing those electrodes which are substantially coplanar (as well as those which are fully co planar. Thus, individual electrodes can be slightly raised, recessed, and/or angled as compared other coplanar electrodes 4 and 10 on planar substrates 2 and 8, respectively, and still be considered coplanar.

One or more planar intermediate layers 14 can be disposed in between the opposed first planar surface 6 of the first planar substrate 2 and the second planar surface 12 of the second planar substrate 8. The intermediate layer(s) 14 may be formed using a variety of methods and materials known to a person of ordinary skill in the art. For example, intermediate layers 14 may be made out of an inert substrate such as a dielectric, pressure sensitive adhesive, laminate, etc. . . . Alternatively, intermediate layers 14 can be integrated into planar substrates 2, 8, respectively, by forming intermediate layer(s) 14 directly on top of surfaces 6, 12 and coplanar electrodes 4, 10. One or more of intermediate layer(s) 14 can be an isolating layer(s) made from a dielectric or insulating material which isolates one or more, up to all, of electrodes 4 and electrodes 10 from one another. Alternatively, intermediate layers 14 can provide conductive pathways which allow one or more of electrodes 4 and one or more of electrodes 10 to be electrically connected to one another.

In the embodiment depicted in in FIGS. 2-3, test strip 100 contains an intermediate layer 14B which defines a fluid flow path 16. The flow path 16 allows fluid to flow from the inlet 18 to the outlet 20 of test strip 100.

Test strip 100 may also contain intermediate layers 14A and 14C disposed on opposing planar sides of the intermediate layer 14B. Intermediate layers 14A and 14C may define one or more sensing areas 22. Individual sensing areas 22 allow fluid traveling through the fluid flow path 16 to come into contact with individual coplanar electrodes 4, 10 on the first or the second planar substrate 2, 8. For example, the sensing areas depicted in FIGS. 1-3 are circular apertures which extend through the respective intermediate layers 14A and 14C. Sensing areas 22 may also be fully or partially filled with a chemical/reagent 38 which may react with fluid in the fluid flow path 16 and produce a detectable analyte. Alternatively, individual sensing areas 22 may also be defined without the need for intermediate layers 14A and 14C by applying chemicals and/or reagents directly on a coplanar electrode 4, 10.

Planar substrate 2 is shown in FIGS. 1-3 as having individual sensing areas 22—that are adjacent to the first planar surface 6 of the first planar substrate 2—that are associated with respective, individual coplanar electrodes 4 on the first planar surface 6 (illustrated in FIGS. 1 and 2 in dotted lines as they are not directly visible from that view). Similarly, individual sensing areas 22 adjacent to the second planar surface 12 of substrate 8 are associated with respective, individual coplanar electrodes 10. Those individual coplanar electrodes 10 associated with a sensing area 22 are identified as coplanar electrodes 10A in FIGS. 1-3. The second planar surface 12 of substrate 8 further contains coplanar electrodes 10, identified as coplanar electrodes 10B in the Figures, that are not associated with a sensing area 22 adjacent to the second planar surface 12 of substrate 8.

As best shown in FIGS. 2-3, one or more, up to all, of the individual coplanar electrodes 10B of the second planar surface 12 of the second planar substrate 8 are electrically connected to a coplanar electrode 4 on the first planar surface 6 via a conductive element 24. Conductive elements 24 extend between the first planar surface 6 and the second planar surface 12 without passing through the first planar substrate 2 or the second planar substrate 8. The conductive element 24 may also extend between the first planar surface 6 and the second planar surface 12 without passing through intermediate layer(s) 14. Alternatively, conductive element 24 may pass through one or more, up to all, of intermediate layer(s) 14. As best shown in FIG. 3, the conductive element 24 extends, at least partially, in a direction that is substantially perpendicular to the first planar surface and the second planar surface.

The conductive element 24 may be formed using a variety of methods and materials known to a person of ordinary skill in the art. For example, conductive element 24 may be a pogo pin, a wire, or a deposit of conductive metal. It should also be appreciated that conductive element may be affixed to one or both of the first planar substrate 2 and the second planar surface 8. For example, an exemplary conductive element 24 may be affixed to the first planar substrate 2 prior to the assembly of test strip 100 such that, when assembled, the conductive element 24 comes into electrical contact with exemplary coplanar electrodes 10B (or vice versa). The conductive element 24 may also be affixed to one or both of to one or both of the first planar substrate 2 and the second planar surface 8 after they are arranged in the opposing configuration depicted in FIGS. 2-3. Additionally, when the conductive element 24 passes through one or more, up to all, of intermediate layers 14, the conductive element 24 may be formed in the one or more intermediate layers 14 prior to arranging the first planar substrate 2 and the second planar surface 8 in the opposing configuration depicted in FIGS. 2-3.

As best shown in FIG. 2, the area of the first planar surface 6 of the first planar substrate 2 and the intermediate layer(s) 14 are both smaller than the second planar surface 12 of the second planar substrate 8. When placed in an opposing configuration, the size difference leaves an exposed portion 26 of the second planar surface 12 of the second planar substrate 8 uncovered by the first planar substrate 2 as well as intermediate layer(s) 14. The exposed portion 26 contains a portion of coplanar electrodes 10 (which may be referred to as coplanar electrical contacts 28). The coplanar electrical contacts 28 of the exposed portion 26 may then be interfaced with an associated medical instrument (such as a meter or reader) by inserting the exposed portion 26 into a receiving slot in the medical instrument (not shown). Stated differently, when viewing the test strip 100 from above the first planar surface 6 of the first planar substrate 2 along the line extending from the first planar surface 6 of the first planar substrate 2 to the second planar surface 12 of the first planar substrate 2, the exposed portion 26 of the second planar substrate 8, and the coplanar electrical contacts 28 located thereon, are left uncovered by the first planar substrate 2 and the intermediate layers 14.

In yet another alternative embodiment of test strip 100, the first planar substrate 2 of test strip 100 can be replaced by a simple lid that is devoid of electrodes. This configuration would necessitate a test strip 100 in which the second planar substrate 8 contains the only group of coplanar electrodes 10A.

Figure 4:
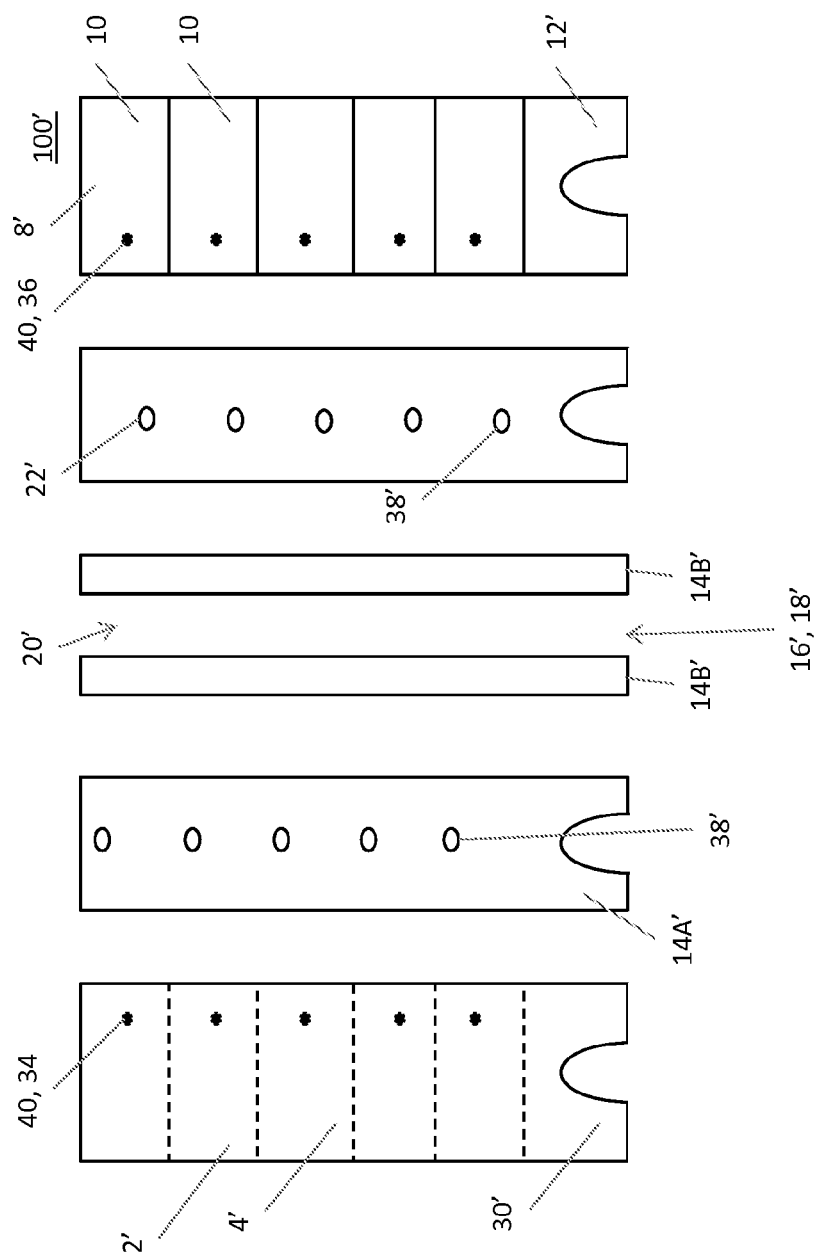
FIG. 4 depicts an exploded view of a second embodiment of the test strip.
Figure 6:
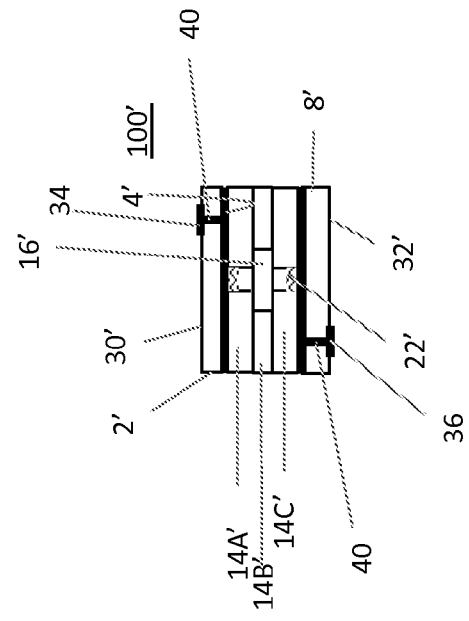
FIG. 6 depicts a side view of the second embodiment of the test strip.
Figure 5:
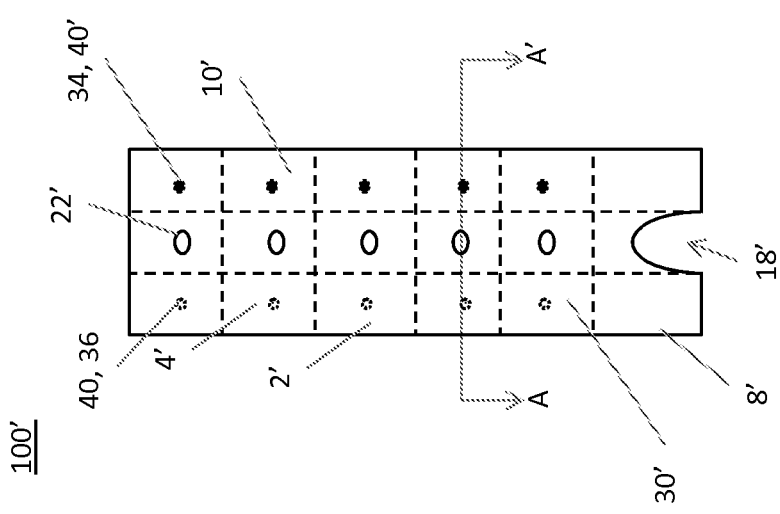
FIG. 5 depicts a top view of test strip of the second embodiment of the test strip.

FIGS. 4-6 depict a second illustrative embodiment of a test strip according to the inventive concepts disclosed herein. FIG. 4 depicts an exploded view of each layer of test strip 100'. FIG. 5 depicts a top view of test strip 100'. FIG. 6 depicts a side view of test strip 100' along line A-A'. In the following description of test strips 100', it should be noted that similar reference numbers to those used to describe test strip 100 in FIGS. 1-3 are intended to refer to similar features—thus avoiding the need to duplicate the detailed description of those features.

As best shown in FIGS. 4-5, the first planar substrate 2' and the second planar substrate 8' have a respective second planar surface 30 and 32 which are opposite the first planar surface 6' and the second planar surface 12' of the first planar substrate 2' and the second planar substrate 8', respectively. One or more, up to all, of the individual coplanar electrodes 4' and 10' of the first planar surface 6' and the second planar surface 12' of the first planar substrate 2' and the second planar substrate 8', respectively, are electrically connected to a respective electrical contact 34 and 36 located on the respective second planar surface 30 and 32. Electrical contact(s) 34 may be referred to as "top side contacts" or "front side contacts" while electrical contacts 36 may be referred to as "bottom side contacts" or "back side contacts" (or vice versa depending on the orientation of test strip 100'). Individual coplanar electrodes 4' and 10' can be electrically connected to a respective electrical contact 34 and 36 in a variety of ways. For example, coplanar electrodes 4' and 10' can be electrically connected to a respective electrical contact 34 and 36 using vias, otherwise known as through-holes, that have a conductive element 40 located therein that electrically couples respective coplanar electrodes 4' and 10' to electrical contact 34 and 36. Test strip 100' can thus be interfaced with a test strip reading device configured to accept a test strip with top side contacts 34 and bottom side contacts 36.

Figure 7:
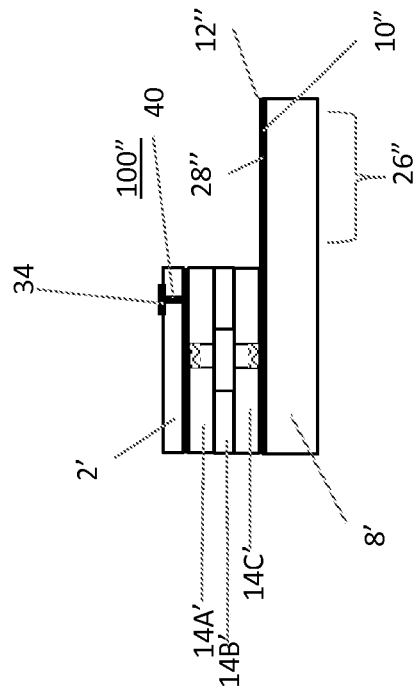
FIG. 7 depicts a side view of a third embodiment of a test strip.

In yet another alternative configuration, FIG. 7 depicts a side view of test strip 100" along a hypothetical line A-A'. In test strip 100", a top side contact 34 is located on planar substrate 2 while the exposed portion 26" of the second planar substrate 8" contains a portion of coplanar electrodes 10" (e.g., coplanar electrical contacts 28"). This configuration allows the contacts 34 and 28" of test strip 100" to be accessed from the same side (e.g., the top side).

A person of ordinary skill in the art should also appreciate that there are a variety of methods which may be used to manufacture the test strip 100 and 100', as described above. For example, intermediate layer(s) 14 and then the second planar substrate 8 may be formed on the first planar substrate 2 (or vice versa).

What is claimed is:

1. A test strip comprising:
   a first planar substrate with coplanar electrodes on a first planar surface and a second planar substrate with coplanar electrodes on a second planar surface, the first planar substrate and the second planar substrate being arranged such that the first surface of the first planar substrate opposes the second planar surface of the second planar substrate;
   an intermediate layer disposed in between the opposed first surface of the first planar substrate and the second planar surface of the second planar substrate;
   the first planar surface of the first planar substrate having a first sensing area electrically connected to a first electrical contact; and
   the second planar surface of the second planar substrate having a second electrical contact electrically connected to the first electrical contact via a conductive element, the conductive element extending between the first surface of the first planar substrate and the second surface of the second planar substrate without passing through the first planar substrate or the second planar substrate.

2. The test strip of claim 1, wherein the second electrical contact is electrically connected to the conductive element without passing through the intermediate layer.

3. The test strip of claim 1, wherein the second planar surface of the second planar substrate further comprises a second sensing area electrically connected to a third electrical contact; and
   wherein the second electrical contact on the second planar substrate is not electrically connected to a sensing area on the second surface of the second planar substrate.

4. The test strip of claim 1, wherein the area of the first surface of the first planar substrate is smaller than the second planar surface of the second planar substrate thereby leaving a portion of the area of the second surface of the second substrate uncovered by the first surface of the first planar substrate; and wherein a portion of the second electrical contact is located in the uncovered portion of the second surface of the second planar substrate.

5. The test strip of claim 1, wherein the conductive element extends in a direction that is substantially perpendicular to the first planar surface and the second planar surface.

6. The test strip of claim 1, wherein the conductive element is a pogo pin, a wire, or a deposit of conductive metal.

7. A test strip comprising:
   a first planar substrate having a first planar surface and a second planar surface;
   a first conductive layer formed on the second planar surface of the first planar substrate, the first conductive layer forming a first electrical contact;
   a second planar substrate having a first planar surface and a second planar surface, the second planar substrate being disposed below the first planar substrate along a line extending from the first planar surface of the first planar substrate to the second surface of the first planar substrate, the first planar surface of the second planar substrate facing the second surface of the first planar substrate, the first and second planar surfaces of the second planar substrate having a larger surface area than the area of both the first and second planar surfaces of the first planar substrate;
   a second conductive layer formed on the first planar surface of the second planar substrate, the second conductive layer comprising a second electrical contact;
   a first planar intermediate layer disposed in between the second surface of the first planar substrate and the first surface of second planar substrate, the first planar intermediate layer defining a fluid flow path configured so that when a liquid is flowing through the fluid flow path the liquid is in fluidic contact with at least part of the first electrical contact and at least part of the second electrical contact, the first and second planar surfaces of the first planar intermediate layer having a smaller surface area than the area of the first and the area of the second planar surfaces of the first planar substrate as well as the area of the first and the area of the second planar surfaces of the second planar substrate;
   wherein when viewing the sensor assembly from above the first surface of the first planar substrate along the line, a portion of the second planar substrate and the second electrical contact are uncovered by another layer of the assembly; and
   a conductive element electrically connects the first electrical contact to the second electrical contact without passing through the first planar substrate or the second planar substrate.

* * * * *